United States Patent
Steer

[11] Patent Number: 5,709,674
[45] Date of Patent: Jan. 20, 1998

[54] OSTOMY COUPLING

[75] Inventor: Peter L. Steer, Sussex, England

[73] Assignee: E.R. Squibb & Sons, Inc., Princeton, N.J.

[21] Appl. No.: 612,707

[22] Filed: Mar. 8, 1996

[30] Foreign Application Priority Data

Mar. 9, 1995 [GB] United Kingdom ............. 9504766

[51] Int. Cl.⁶ ..................................................... A61F 5/44
[52] U.S. Cl. ........................................ 604/342; 604/332
[58] Field of Search ................................ 604/332–345

[56] References Cited

U.S. PATENT DOCUMENTS 4,931,045  6/1990  Steer ..................................... 604/338

FOREIGN PATENT DOCUMENTS

2179556  3/1987  United Kingdom ............. 604/332
9323229  11/1993  WIPO ............................ 604/332

Primary Examiner—Robert A. Clarke
Attorney, Agent, or Firm—Stuart E. Krieger

[57] ABSTRACT

An ostomy coupling includes a first coupling ring attached to a medical grade adhesive pad, a second coupling ring attached to an ostomy pouch, and an intervening ring. The intervening ring is slidable along the lower portion of the cylindrical wall of the first coupling ring. The intervening ring is also finger-engageable so as to facilitate the pushing together of the first and second coupling rings into a coupling arrangement while minimizing pressure on the stomal area.

6 Claims, 7 Drawing Sheets

OSTOMY COUPLING

BACKGROUND OF THE INVENTION

This invention relates to an ostomy coupling.

Such couplings are known. A successful design is described and illustrated in U.K. Patent No. 1,571,657. Such an arrangement allows a bag to be removed and replaced without detaching the pad from the body of the wearer, for example to allow the bag to be emptied or discarded.

Some wearers suffer pain or discomfort when re-attaching a bag or attaching a fresh bag, because it is normally necessary to apply some force in a direction towards the wearer's body in order to interengage the coupling elements. As the peristomal area and the stoma are usually tender, any force applied as described above gives rise to discomfort or pain. Efforts have been made to reduce or solve this problem by devising constructions which are intended to allow the wearer to place his or her fingers or thumbs behind a part of the appliance, with the aim of limiting transmission to the peristomal region of the force which must be applied to connect the coupling elements together. One suggested construction is described in GB Patent No. 2,115,288 (Hollister). This attempted solution suffers from various defects. Firstly the area of the stomal orifice is restricted because the inner periphery of a thin annular flexible resilient web extends into and restricts the stomal aperture. It being customary to cut the medical grade adhesive pad with scissors to form a hook to receive the stoma, there is a risk that this may cut the inner edge of the web, in which event leaks may occur. Secondly, the inner edge of this web, being rather sharp, could cause discomfort if it contacts the exposed stoma. Thirdly the use of a thin web in the attachment of the bag to the body side pad (also sometimes called a faceplate) has the result, when the wearer stands or sits upright, that the bag tends to drag or droop downwardly; the impression to the user is that the whole arrangement is less compact and secure than other kinds of ostomy appliance. Fourthly the arrangement inevitably has internal nooks and crannies in which faeces can collect. Fifthly, bearing in mind that ostomy couplings of the kind discussed in this application may have to be made in sizes as small as 38 or 45 mm. diameter, there is little space available for a wearer to insert fingers beneath the web.

Mother example of ostomy coupling was designed by the present inventor and is shown in U.K. Patent No. 2,215,606. One possible disadvantage of this coupling is that inadvertent tilting of a ring relative to a chute member may cause these parts to bind against each other rather than move freely over the designed travel distance.

SUMMARY OF THE INVENTION

It is an aim of the present invention to provide an improved ostomy coupling.

According to one aspect of the invention, there is provided an ostomy coupling having a first coupling ring attachable to a medical grade adhesive pad and a second coupling ring, engageable and disengageable with the first ring, the second ring being attachable to an ostomy pouch, there being a finger-engageable intervening ring loosely disposed between the first and second rings, characterised in that movement of the intervening ring away from the pad is limited by a stop rim which extends radially outwardly of a chute portion of the first coupling ring.

The intervening ring is preferably at least partly upwardly angled so that a wearer of the ostomy coupling can place a finger or thumb behind each of said tabs.

According to another aspect of the present invention, there is provided an ostomy coupling which comprises a first coupling ring attachable to a medical grade adhesive pad and a second coupling ring, connectable to the first ring and attachable to an ostomy pouch, the first coupling ring comprising a flange portion and a wall of closed-loop shape extending substantially perpendicular to the flange and surrounding a stomal orifice, the wall having a radially outwardly-extending rim at its edge further from the flange, characterised in that the first coupling ring carries thereon a relatively rigid third ring which is slidable in an axial direction relative to the first ring, there being, interposed between the third ring and that part of the first coupling ring which is closest to the second coupling ring, a stop means on the first ring for limiting movement of the third ring relative to the first coupling ring.

The function of the third ring is to provide an annular support surface under which the wearer may place his/her fingers (or thumbs) when coupling the first and second rings together, or when separating them. The third ring enables this to be done without applying a painful pressure to the peristomal area. This may be achieved, in practice, by the wearer placing one thumb behind the third coupling ring, and with, for example, the first and second fingers of each hand, pressing the bag side coupling member towards the respective thumbs. If necessary, one can repeat this procedure working around the periphery of the coupling. The third ring does not play any part in maintaining the two coupling rings connected together. Its internal diameter is such that, once on the other joined coupling, it can easily and loosely rotate relative to the coupling. In a preferred embodiment of the invention, the rings are substantially circular, but, without departing from the invention, they could be oval or other closed-loop shape. In this specification, the word "ring" is to be construed as not limited to a circular part. While the preferred embodiment of the invention has a pouch or bag connected to the second ring and an adhesive body-attachable pad connected to the first ring, a converse arrangement is possible and is considered within the invention.

As regards the intervening or "third" ring, this need not be peripherally continuous. It could be a split or a broken ring, e.g. generally circular but with the ends of the broken ring joinable by a suitable catch or connecting arrangement, such, for example, as seen in our U.S. Pat. No. 4,850,985 or in FIG. 5 of our U.S. Pat. No. 4,755,177.

In an advantageous embodiment of the invention, belt lugs and a gripping lug are attached to or preferably moulded integral with the second coupling ring. While the inclusion of such lugs in an ostomy coupling is well-known, the particular arrangement illustrated herein allows a quick and trouble-free "peel off" separation of pouch from pad when this is desired, e.g. when it is necessary to discard a full pouch and attack a fresh one.

According to an advantageous but optional feature of the invention, the second coupling ring may be channel-shaped in cross-section and may have a flat flange extending radially outwardly from its radially outer wall. One advantage of such a flat flange is that it increases the contact area available between the pouch wall and the second coupling ring.

BRIEF DESCRIPTION OF THE DRAWINGS

The invention will be better understood from the following description of a non-limiting embodiment thereof, given with reference to the accompanying drawings, in which like parts are represented by like numerals. In the accompanying drawings.

DETAILED DESCRIPTION OF THE DRAWINGS

Figure 1:
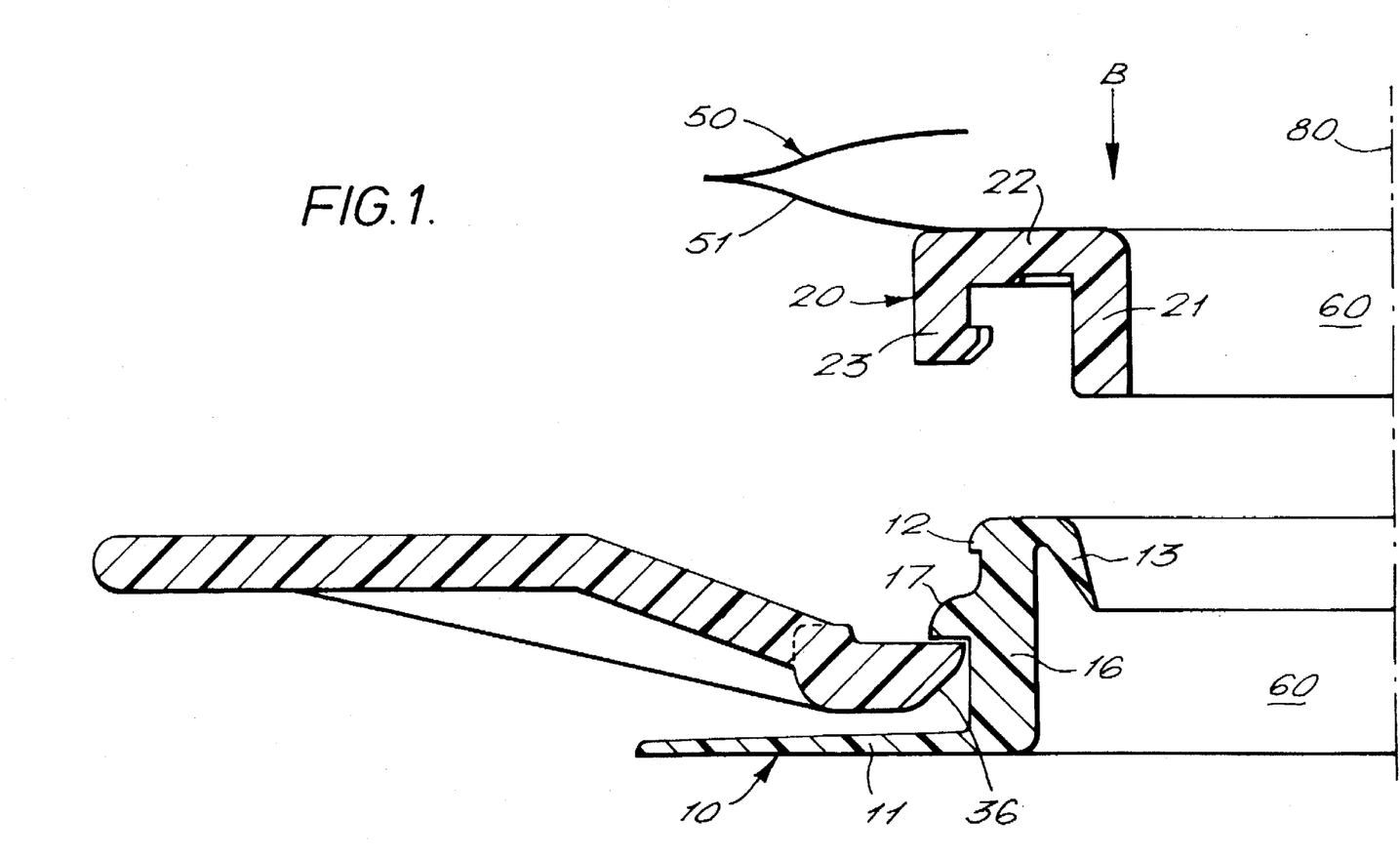
FIG. 1 is a cross section, showing one end of a diameter only, of one example of ostomy coupling according to the invention, the parts being shown in separated condition.
Figure 2:
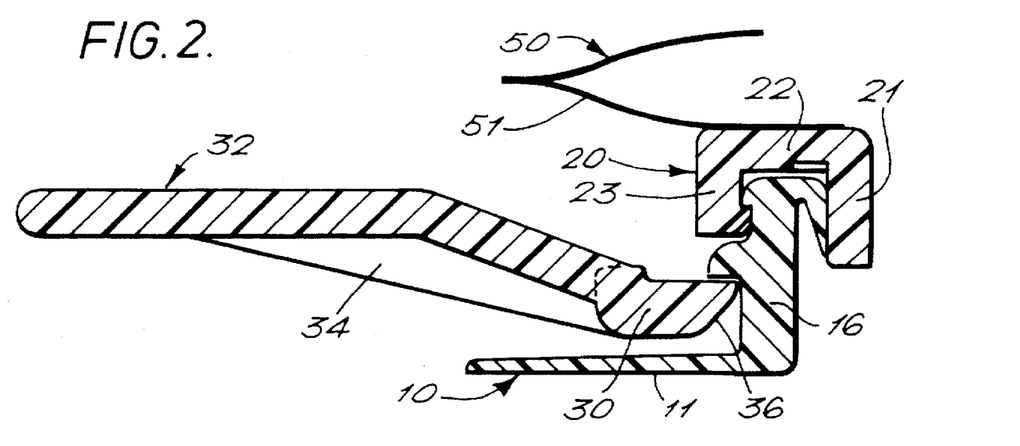
FIG. 2 is a view similar to FIG. 1 but showing the parts in their mutually coupled condition.

Referring firstly to FIGS. 1 and 2, which illustrate one embodiment of the invention, a first coupling ring 10 has a flange 11 by which it may be attached to a pad of medical grade adhesive. The ring 10 encircles a stomal orifice 60. The ring 10 has a generally cylindrical wall 16 which surrounds the stomal orifice 60 and at its end which will be nearer to the second coupling ring 20 in use, it has an outwardly extending rim 12 and an inwardly extending deflectable sealing strip 13. On the radially external surface of the cylindrical wall 16 is disposed an outwardly extending rim 17 (also called a stop-means herein) which has a curved upper and outer surface 17A (FIG. 3A) and a flat surface 17B substantially perpendicular to the axis 80 of the coupling.

Figure 3:
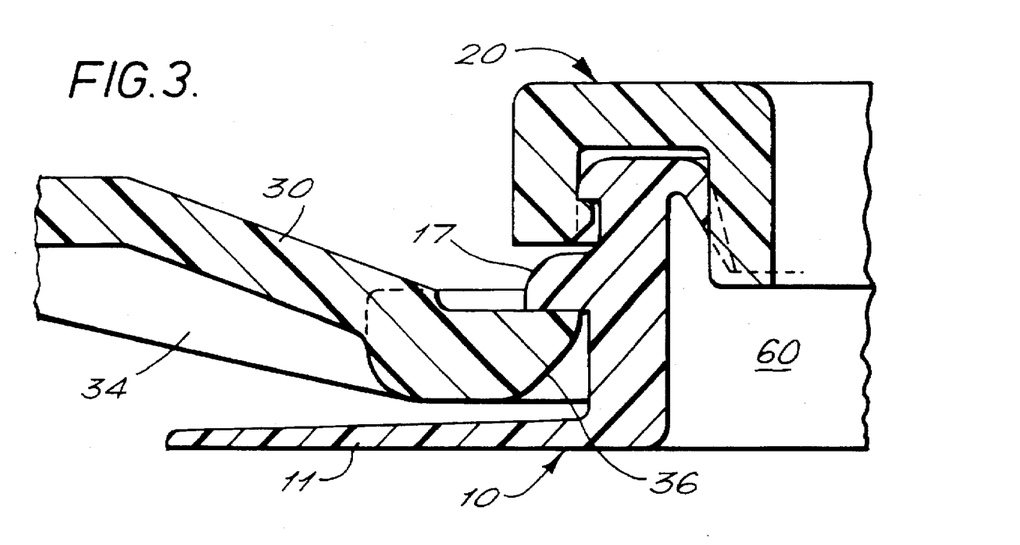
FIG. 3 is a view similar to FIG. 2 of a second embodiment of the invention illustrating (dotted) the normal rest position of the seal strip on the first (body-side) coupling ring and (full-line) the deformed position of the seal strip.
Figure 3A:
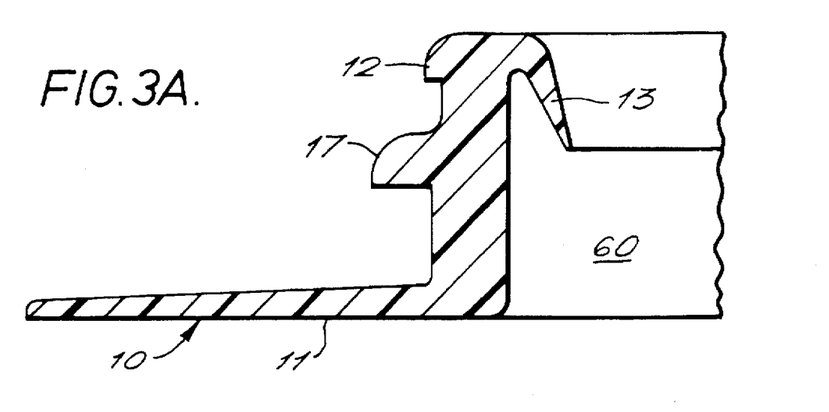
FIG. 3A shows a body-side coupling ring.

The second coupling ring 20, seen in FIGS. 1–3, is of channel shape in cross section and has a generally cylindrical inner wall 21, a base 22, and an outer wall 23. One wall 51 of an ostomy pouch 50 is attached in any suitable way to the surface of the base 22. Belt lugs 224 are connected to or are moulded integrally with the second coupling ring 20. The belt lugs 224 may for example be positioned at the peripheral locations seen in FIG. 12.

A third coupling ring 30 is mounted so as to be slidable to a limited extent relative to the first coupling ring 10. This limited movement is desirable because it makes it easier for a wearer to place fingers or thumbs beneath tabs 32 of the ring 30. The limited movement is terminated by the ring 30 encountering the rim 17. Hence the force applied by fingers or thumbs to effect this movement is transmitted to the head part of the coupling ring 10 and thence to the surface at he base of the channel-section coupling ring 20. That is, the squeezing pressure achieved by the thumbs (or fingers) lifting the ring 30, and the fingers (or thumbs as the case may be) applying pressure to the bag 50 and through it to the second coupling ring 20, assures that the coupling parts 10, 20 are securely joined together, and at the same time pressure on the sensitive stoma or peristomal area is minimised.

Figure 13:
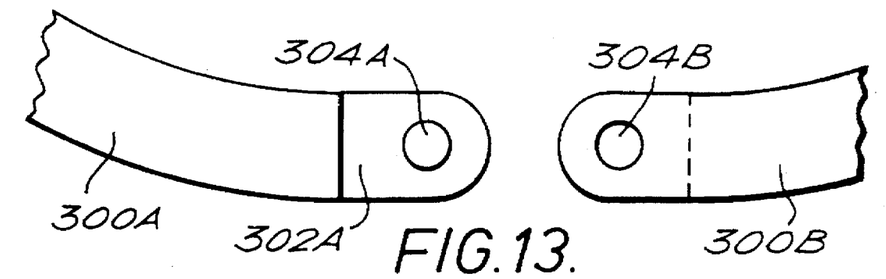
FIG. 13 is a top plan view of an arrangement for joining the ends of a split ring.
Figure 14:
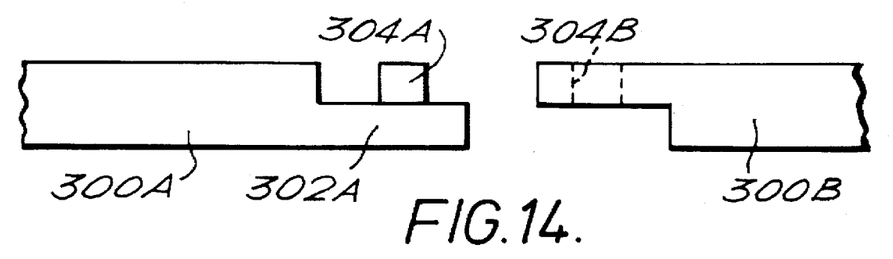
FIG. 14 is a side elevational view of the joining arrangement of FIG. 13.

The third ring 30 is made up of a closed loop, usually circular, ring portion 32. Tabs 32 may be located at each end of a single diameter of the ring 30. Alternatively the ring 30 may be a complete annulus of width about 19 to 32 mm. (¾ to 1¼ inches). The ring 30 need not be a complete closed loop. It could be a split ring, the ends being joined for example by an arrangement such as is illustrated in FIGS. 13 and 14. The ring 30 is preferably made of relatively rigid plastics material for example an acetal resin. The tabs 32 of the ring 30 are formed in a manner such that they are in part slightly angled upwardly (or bent out of a plane perpendicular to the axis of the coupling) so providing space beneath which a finger or thumb of the wearer of the coupling can be placed, in order to provide a support or reaction point and so prevent pain or discomfort to the wearer when the rings 10 and 20 are fitted together. A pair of strengthening ribs 34 are advantageously included, see FIGS. 6 and 7. As will be understood, in the course of connecting the second coupling ring 20 to the assembly constituted by rings 10 and 30, an initial force is applied in the direction of the arrow B seen in FIG. 1. Absent the ring 30 and its tabs 32, a substantial part of this force will be transmitted to the body of the wearer and will cause pain and discomfort in the normally very tender peristomal area.

Figure 4:
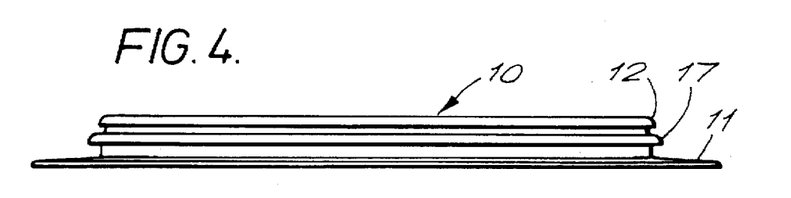
FIG. 4 is a side elevational view of the coupling ring shown in FIG. 3A.
Figure 5:
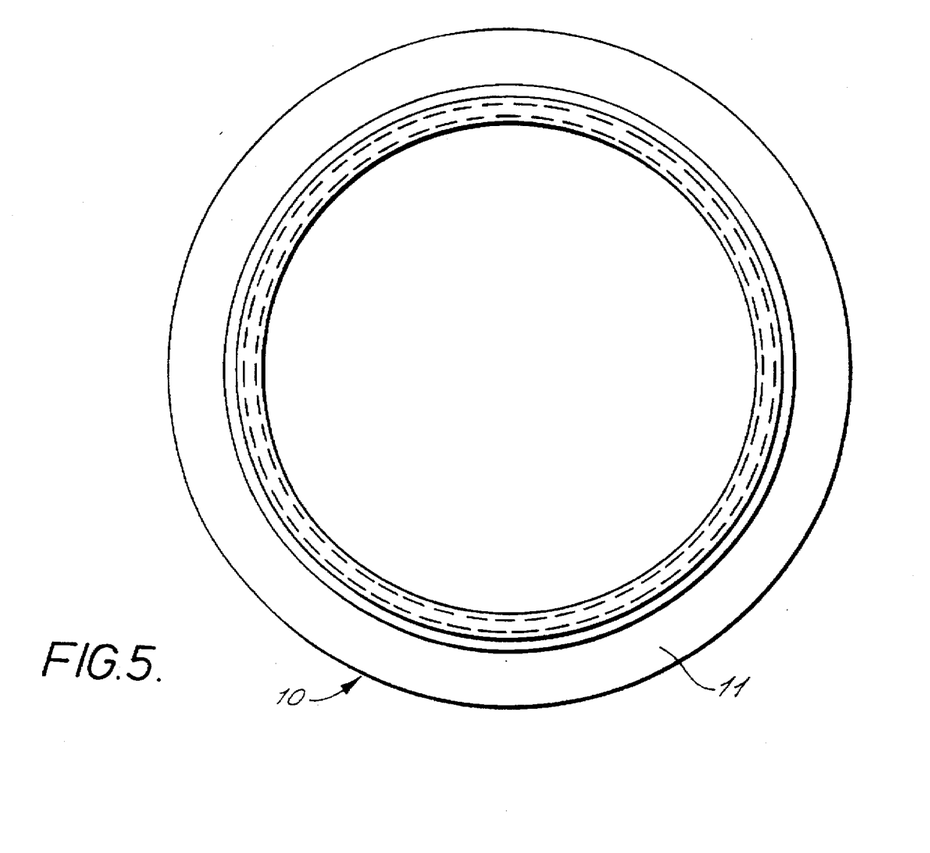
FIG. 5 is a top plan view of the coupling ring shown in FIG. 3A.

The assembled condition of the parts is seen in FIG. 3. The coupling together of the coupling rings 10 and 20 is carried out in the manner described below with reference also to FIGS. 3A, 4 and 5. Firstly the pouch attached to the second coupling ring 20 is brought towards (see arrow B, FIG. 1) the body side coupling ring 10. The wearer then places his thumbs beneath the tabs 32.

As will be understood the provision of the tabs 32 enables the person who is seeking to mount an ostomy pouch on his body side coupling ring to place his (or her) thumbs under the tabs 32 and use the fingers to push the bag side coupling ring 20 axially towards the abdomen.

The ring 30 is freely rotatable relative to the first coupling ring 10. According to one procedure, by rotating the third ring 30 in successive steps, relative to the first ring 10, which is effectively fixed because it is mounted on the medical grade adhesive pad secured to the abdomen, and in each position pressing on the first and second coupling ring in the manner described, it is possible to cause the two rings 10 and 20 to engage at successive peripheral regions.

Figure 6:
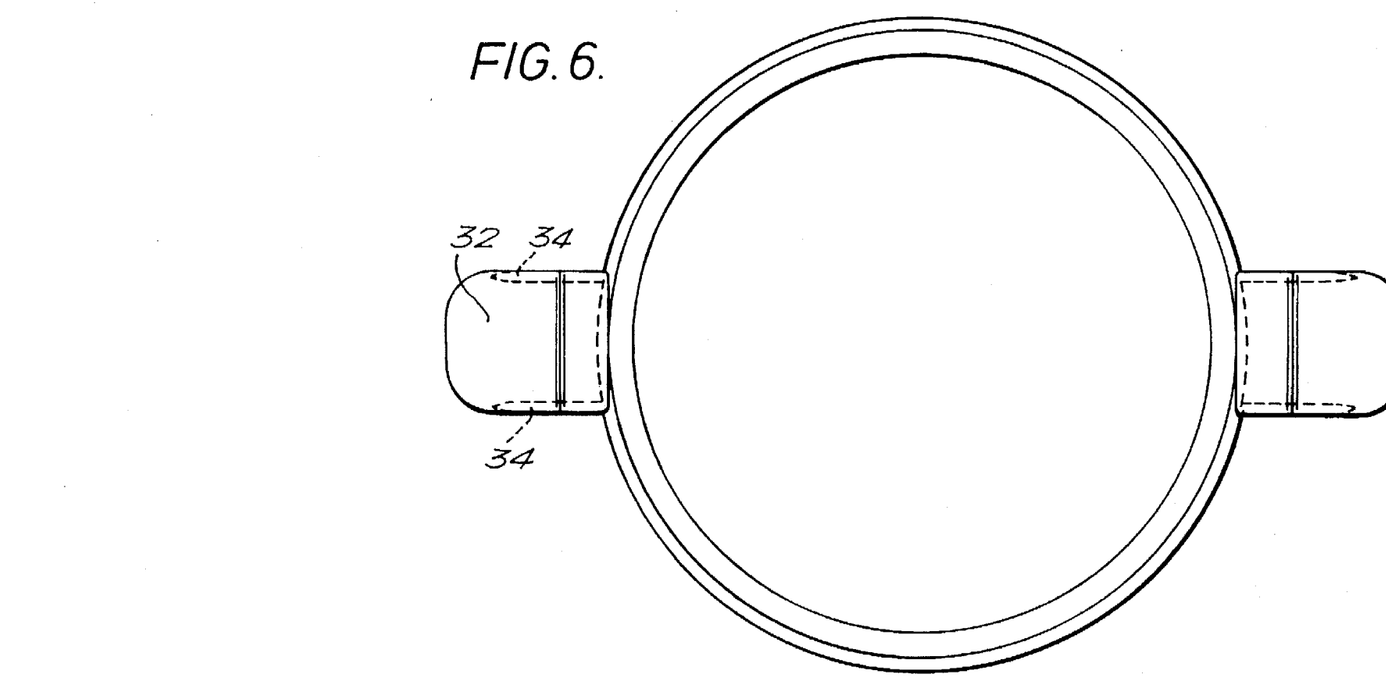
FIG. 6 is a top plan view of the intervening ring.
Figure 7:
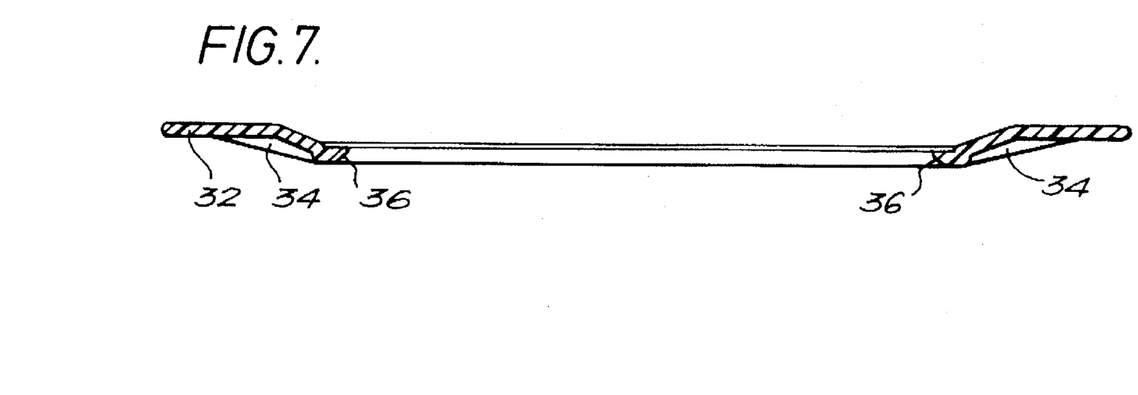
FIG. 7 is a cross-sectional view of the intervening ring of FIG. 6.
Figure 8:
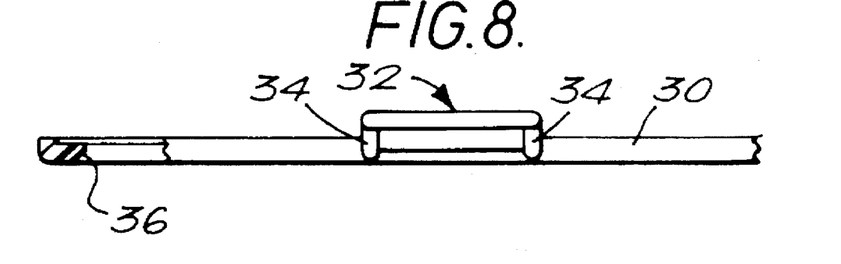
FIG. 8 is an elevational view of a portion of the intervening ring of FIG. 6.

The inner lower edge of the third ring 30 is rounded or chamfered (at 36, see FIGS. 6 and 8) so that the ring 30, being made of deformable plastics material, can be "sprung" or forced past the rim 17 on the coupling ring 10. This is done in assembling the ring 30 onto the body-side coupling 10 for the first time, prior to attaching the bag 50 (and coupling ring 20) to ring 10. As seen in FIG. 6, the tabs 32 slope upwardly (e.g. at 20 degrees) relative to the plane of the ring, and then extend radially outwardly relative to said plane. However, other configurations may be employed.

Figure 9:
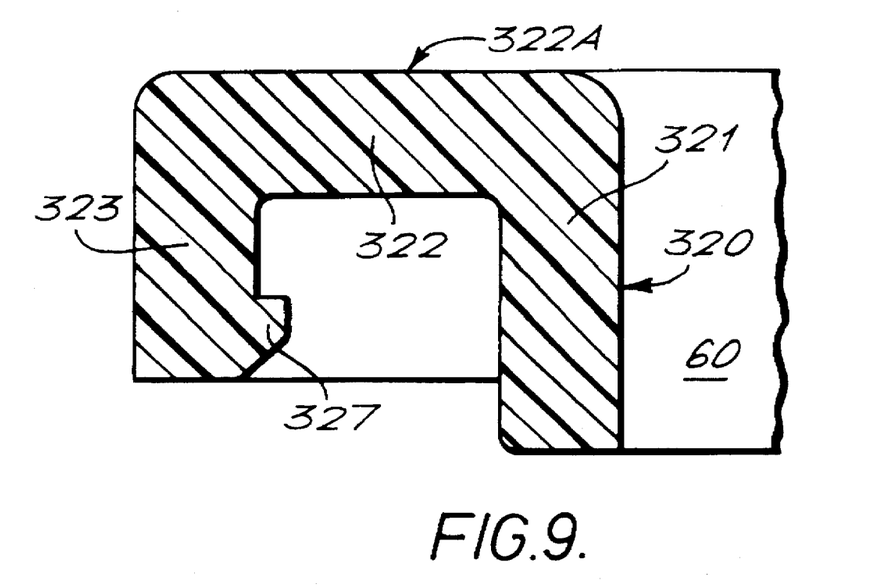
FIG. 9 is a cross sectional view, at one end of a diameter, illustrating a second (bag-side) coupling ring of channel shape as seen in cross section.

Referring now to FIG. 9, this illustrates a bag-side coupling of annular channel-section form having a base 322, a base surface 344 to which a wall of an ostomy bag is attached, and inner and outer generally cylindrical walls 321 and 323. An overhanging rim 227 extends around the circumference of the ring 320. This bag-side coupling is designed to co-operate with the body-side coupling 10 illustrated in FIG. 1. The connection between the bag-side and body-side coupling rings is independent of the third ring. In effect, the third ring serves as a force-absorbing member for a limited time when the wearer is placing th bag-side ring onto the body-attached ring. The third ring does not lock or connect the two coupling rings together.

Figures 10, 11, 12:
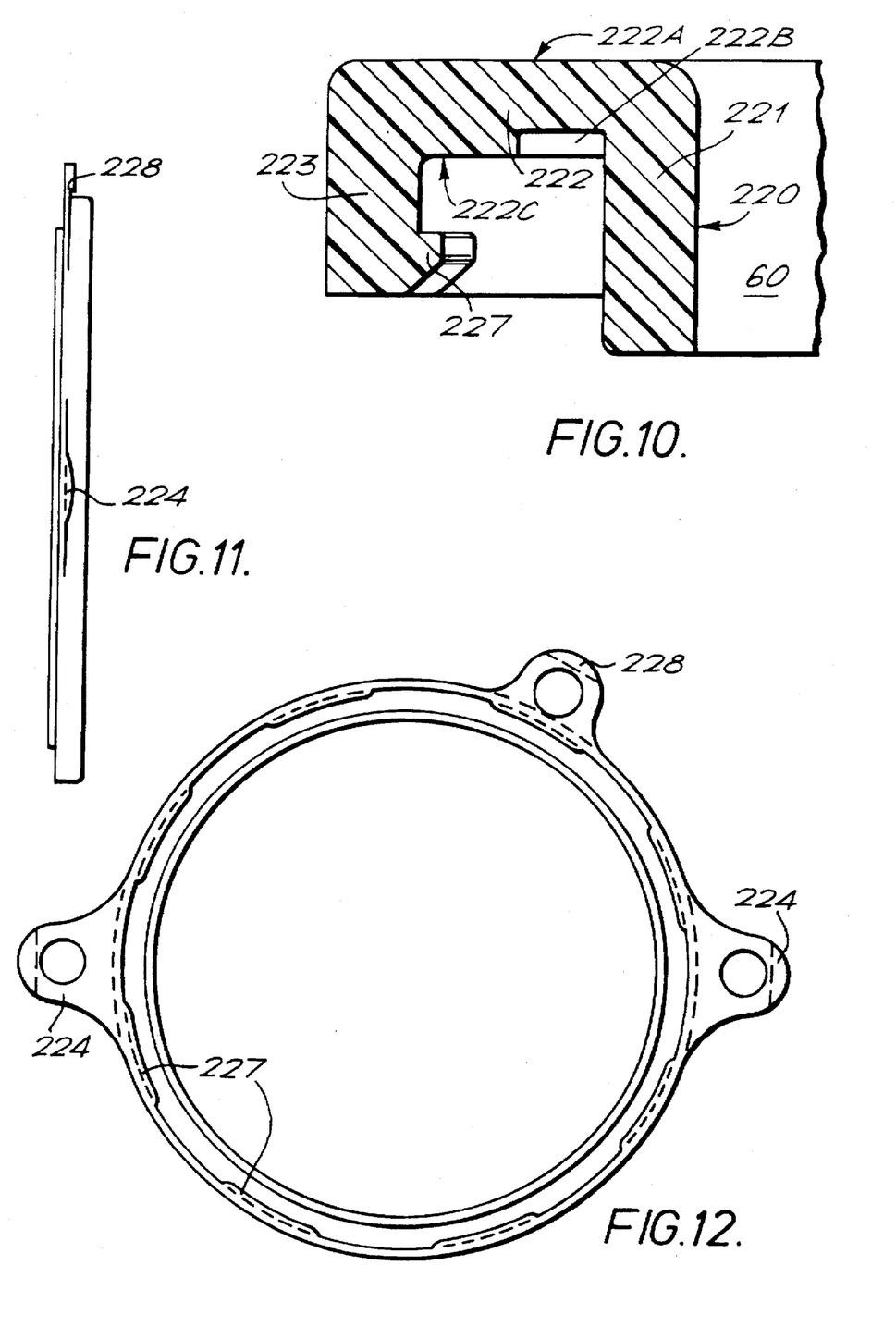
FIG. 10 is a view similar to FIG. 9 but showing in greater detail a second coupling ring according to the first embodiment of the invention.
FIG. 11 is a side view of the coupling ring shown in FIG. 10.
FIG. 12 is a plan view of the coupling ring of FIG. 10 but also showing a pair of tabs thereon.

FIGS. 10–12, like FIGS. 1 and 2, illustrate an embodiment of the invention wherein the third ring 30 is as described in the preceding description, but the first and second coupling rings are designed in accordance with the invention described and claimed in our U.S. patent application Ser. No. 08/335,839, the contents of which are hereby incorporated in this application. Briefly explained, the coupling ring 220 (FIG. 10) has a series of recesses 222B in its base surface 222C. These are equally angularly spaced around the ring 220. Their purpose is to receive mould core members (such as the mould core members referred to as 123 in the aforesaid U.S. application) which serve, during extraction from the mould, to prevent rotation of the coupling ring relative to the mould core member. The coupling ring 20 also has radially-inwardly projecting portions 227 (FIG. 10) which are equally angularly spaced around the coupling ring 220. As explained in the said PCT application, this structure is provided (i) to achieve a secure interlock between rings 10 and 20 and (ii) so that the portions 227 are forced radially outwardly during extraction from the mould by rotation of the core, so permitting the coupling ring 220 to be readily removed. The "overhanging" portions 227 are in an intermittent or castellated arrangement as can be seen in FIG. 12. While 8 portions 227 are illustrated, instead 4 or 12 or 16 or any other suitable number could be included.

Figure 15:
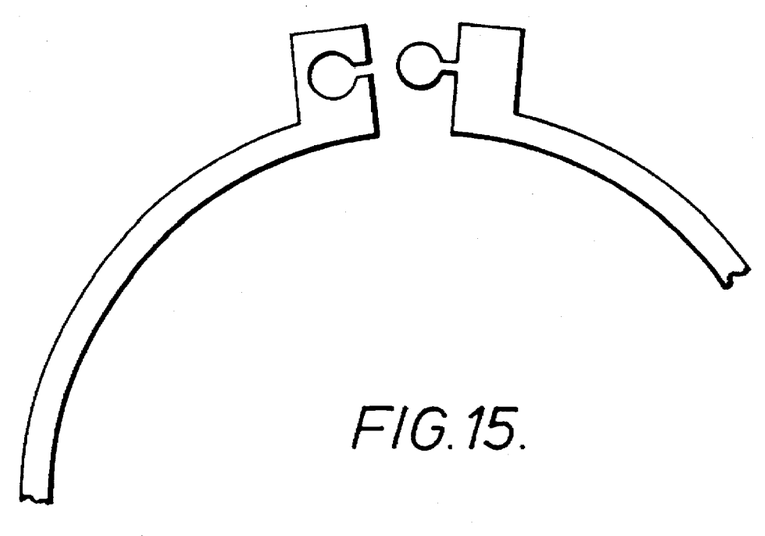
FIG. 15 illustrates another arrangement for connecting the ends of a split ring.

Reference has been made above to the use of a split ring instead of the closed loop ring 30. According to alternative embodiments of the invention, such a split ring (300) may be constructed as shown in FIGS. 13 and 14, or as shown in FIG. 15. Other forms of connection are of course possible.

In FIGS. 13 and 14 the ends of the split ring 300 are shown at 300A and 300B, on one end there being a tab 302A carrying an upstanding circular spigot 304A which is received in a hole 304B in the other end 300B of the ring.

An alternative manner of connection of the two ends of a split ring 320 is illustrated in FIG. 15. One end 322A has a laterally-extending tab 324A integrally moulded therewith. The tab 324A has a circular hole 326A therein, and a gap 328A exists between parts 330A, 332A, of the tab. The other end 322B of the ring carries a tab 324B from which projects a stalk 328B carrying at its free end a spherical or cylindrical member 326B dimensioned to fit within the hole 326A. Other variations or possibilities will occur to a man skilled in the plastics art.

What is claimed is:

1. An ostomy coupling comprising a first coupling ring attachable to a medical grade adhesive pad and having a chute portion;

a second coupling ring engageable and disengageable with said first ring, said second ring being adapted for attachment to an ostomy pouch, said first coupling ring having a cylindrical wall projecting outwardly away from said adhesive pad, said cylindrical wall having an upper portion, distal to said adhesive pad, capable of attachment to said second coupling, said cylindrical wall having a lower portion, proximate to said adhesive pad, including a groove, said lower portion having a rim extending radially outwardly from said cylindrical wall above said groove, and an intervening ring partly capturable within said groove, said intervening ring being slidable in said groove along said lower portion of said cylindrical wall so as to permit a finger to be placed between said intervening ring and adhesive pad for pushing said intervening ring outwardly, said rim limiting said outward movement of said intervening ring.

2. The ostomy coupling as claimed in claim 1 wherein said intervening ring is angled away from mid adhesive pad.

3. The ostomy coupling as claimed in claim 1 in which the front and second coupling rings are substantially circular.

4. The ostomy coupling as claimed in claim 1 wherein said intervening ring is peripherally continuous.

5. The ostomy coupling as claimed in claim 4 wherein said intervening ring is a circular split ring, and the ends of said split ring are joinable.

6. The ostomy coupling as claimed in claim 1 wherein a belt lug and a gripping lug are attached to said second coupling ring.

* * * * *